US00PP20002P2

(12) United States Plant Patent
Apps

(10) Patent No.: US PP20,002 P2
(45) Date of Patent: May 19, 2009

(54) DAYLILY PLANT NAMED 'DYNAMITE RETURNS'

(50) Latin Name: *Hemerocallis hybrida*
Varietal Denomination: Dynamite Returns

(75) Inventor: Darrel A. Apps, Wild Rose, WI (US)

(73) Assignee: Centerton Nursery, Inc., Bridgeton, NJ (US)

( * ) Notice: Subject to any disclaimer, the term of this patent is extended or adjusted under 35 U.S.C. 154(b) by 7 days.

(21) Appl. No.: 11/979,453

(22) Filed: Nov. 2, 2007

(51) Int. Cl.
*A01H 5/00* (2006.01)

(52) U.S. Cl. ..... Plt./312
(58) Field of Classification Search ..... Plt./321
See application file for complete search history.

(56) References Cited

U.S. PATENT DOCUMENTS

PP13,481 P2 * 1/2003 Apps ..... Plt./312
PP13,499 P2 * 1/2003 Apps ..... Plt./312

OTHER PUBLICATIONS

Anonymous. Hemerocallis Dynamite Returns, available at: http://www.whiteflowerfarm.com/30900–product.html.*

* cited by examiner

*Primary Examiner*—Wendy C. Haas
(74) *Attorney, Agent, or Firm*—Buchanan Ingersoll & Rooney PC

(57) ABSTRACT

A new and distinct *Hemerocallis* cultivar of the semi-evergreen type is provided. The new cultivar is very floriferous and forms attractive ruffled bright rosy pink flowers displaying substantial substance, and a funnel-shaped form over an extended period of time. In U.S.D.A. Hardiness Zone No. 6, blooming commonly begins during late June and commonly ends during mid-September. The new cultivar displays a plurality of fans and a plurality of scapes per fan. In excess of 30 buds commonly are formed per scape. The new cultivar is well suited for growing as distinctive colorful ornamentation in the landscape.

3 Drawing Sheets

Figure 1:
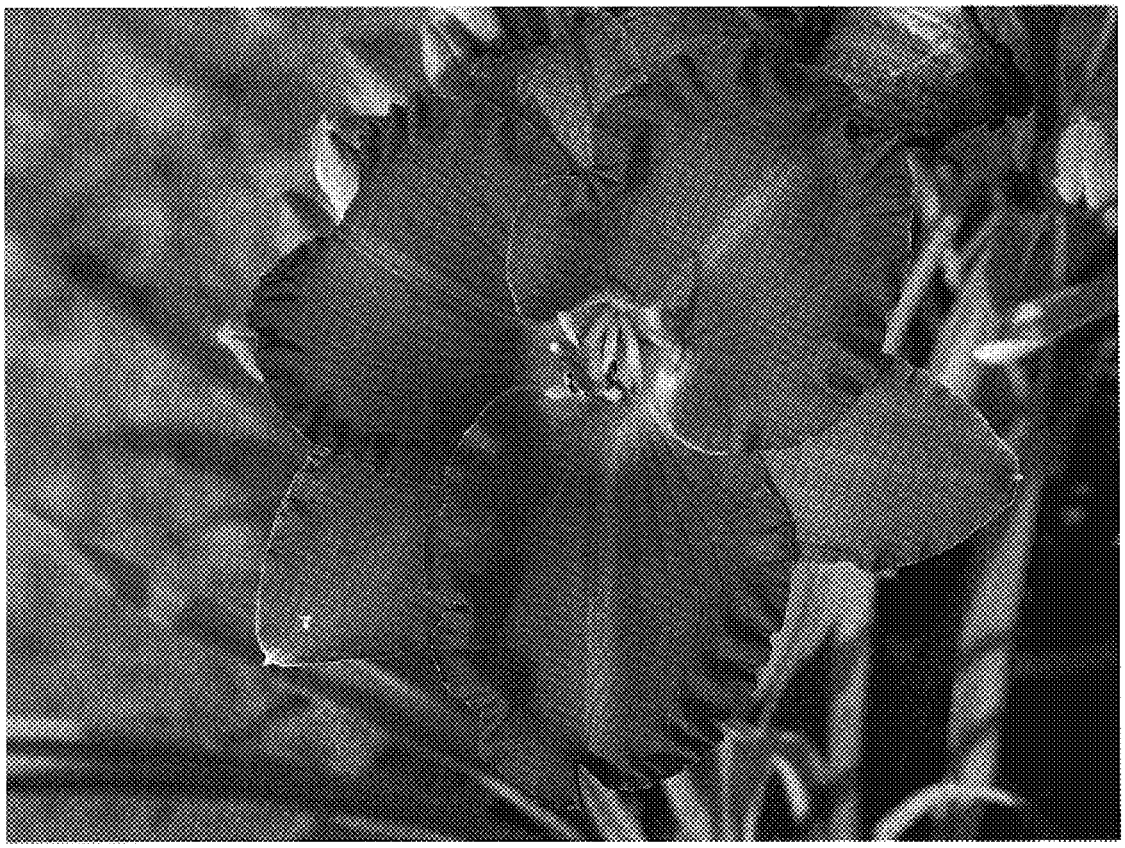

Botanical/commercial classification: *Hemerocallis hybrida*/Daylily.
Varietal denomination: cv. Dynamite Returns.

SUMMARY OF THE INVENTION

The present invention comprises a new and distinct cultivar of *Hemerocallis* plant of the semi-evergreen type, and hereinafter is referred to by the cultivar name 'Dynamite Returns'.

The new cultivar is the product of a planned breeding program which had as its objective the creation of a new Daylily cultivar that is intended for use as attractive ornamentation in the landscape.

The cross that resulted in the production of the new cultivar of the present invention was carried out in a controlled environment during May, 1998, at Bridgeton, N.J., U.S.A. The female parent (i.e., the seed parent) of the new cultivar was the 'Romantic Returns' cultivar U.S. Plant Pat. No. 13,481) which displays rich magenta colored flowers.

The male parent (i.e., the pollen parent) of the new cultivar was the 'Red Hot Returns' cultivar (U.S. Plant Pat. No. 13,499) which displays bright cherry red flowers having a diameter of approximately 12.8 cm on average. Each of the parent plants is registered with the American Hemerocallis Society.

The parentage of the new cultivar of the present invention can be summarized as follows:

'Romantic Returns'×'Red Hot Returns'.

The seeds resulting from the above pollination were sown and small plantlets were obtained which were physically and biologically different from each other. A number of such plants were transplanted into the field at Bridgeton, N.J., U.S.A., during June 1999. Selective study during May 2000 resulted in the identification of a single plant of the new cultivar.

It was found that the new *Hemerocallis* plant of the present invention is of the semi-evergreen type and:

(a) forms attractive ruffled bright rosy pink flowers having substantial substance, and a funnel-shaped form, (b) possesses a long blooming season with repeat blooming, (c) exhibits a propensity to readily display a plurality of fans, (d) readily forms a plurality of scapes per fan over the flowering season, and (e) commonly forms in excess of 30 buds per scape.

The 'Dynamite Returns' cultivar resembles some well-known cultivars, such as the 'Stella D' Oro' cultivar (non-patented in the United States) and the 'Happy Returns' cultivar (non-patented in the United States) in the sense that it commonly possesses an unusually long and substantially continuous blooming season (i.e., a multiple repeat character) of up to 90 days in U.S.D.A. Hardiness Zone No. 6. Such blooming commonly begins during late June and commonly ends during mid-September. This compares to a bloom period of less than about 30 days for over 99 percent of the hybrid Daylilies that are available in the trade.

As indicated, the 'Dynamite Returns' plant exhibits attractive ruffled bright rosy pink flowers that readily can be distinguished from the orange-yellow flowers of the 'Stella D' Oro' cultivar, and the medium yellow flowers of the 'Happy Returns' cultivar. To the best knowledge of the originator, the 'Dynamite Returns' cultivar is the first long and substantially continuously blooming Daylily having flowers that exhibit such a rich pink hue combined with substantial substance.

The new cultivar can form up to 6 or more fans per year. This compares to approximately 6 to 8 fans per year for the 'Stella D' Oro' cultivar and the 'Happy Returns' cultivar. Most Daylily cultivars form only approximately 2 to 3 fans per year. Also, the new cultivar commonly forms several scapes per fan during the flowering season, unlike most Daylilies that commonly produce only one scape per fan.

Asexual reproduction of the new cultivar by division was initially carried out on Aug. 15, 2000 at Bridgeton N.J. U.S.A. At the time of such asexual reproduction the original plant of the new cultivar consisted of a clump of six fans that were phenotypically identical to each other. More specifically, the clump of the new cultivar was removed from the field and the fans were divided. It has been demonstrated that the characteristics of the new cultivar are firmly fixed and are well retained following this asexual reproduction.

The 'Dynamite Returns' plant has not been observed under all possible environmental conditions to date. Accordingly, it is possible that the phenotype may vary somewhat with variations in the environment, such as temperature, light, day length, contact with pesticides, etc.

The new cultivar will be marketed by the Assignee under the HAPPY EVER APPSTER trademark beginning in June, 2008.

BRIEF DESCRIPTION OF THE PHOTOGRAPHS

The accompanying photographs were prepared during August 2003, and show as nearly true as it is reasonably possible to make the same in color illustrations of this character, the original plant and flower of the new cultivar of the present invention. The plant was being grown outdoors in the field at Bridgeton, N.J. U.S.A.

FIG. 1 — illustrates a close view of a mature bright rosy pink flower wherein the stamens and pistil are visible.

Figure 2:
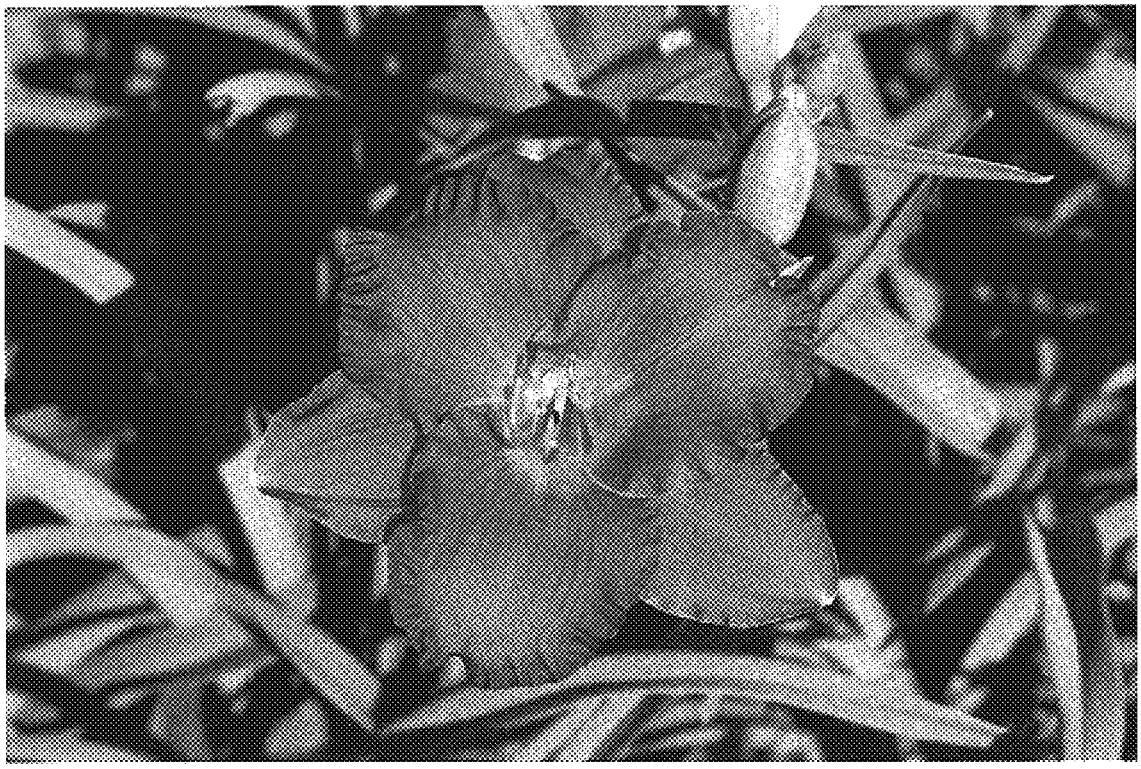

FIG. 2 — illustrates a view of a similar mature flower of the present invention wherein some unopened floral buds and foliage additionally are shown.

Figure 3:
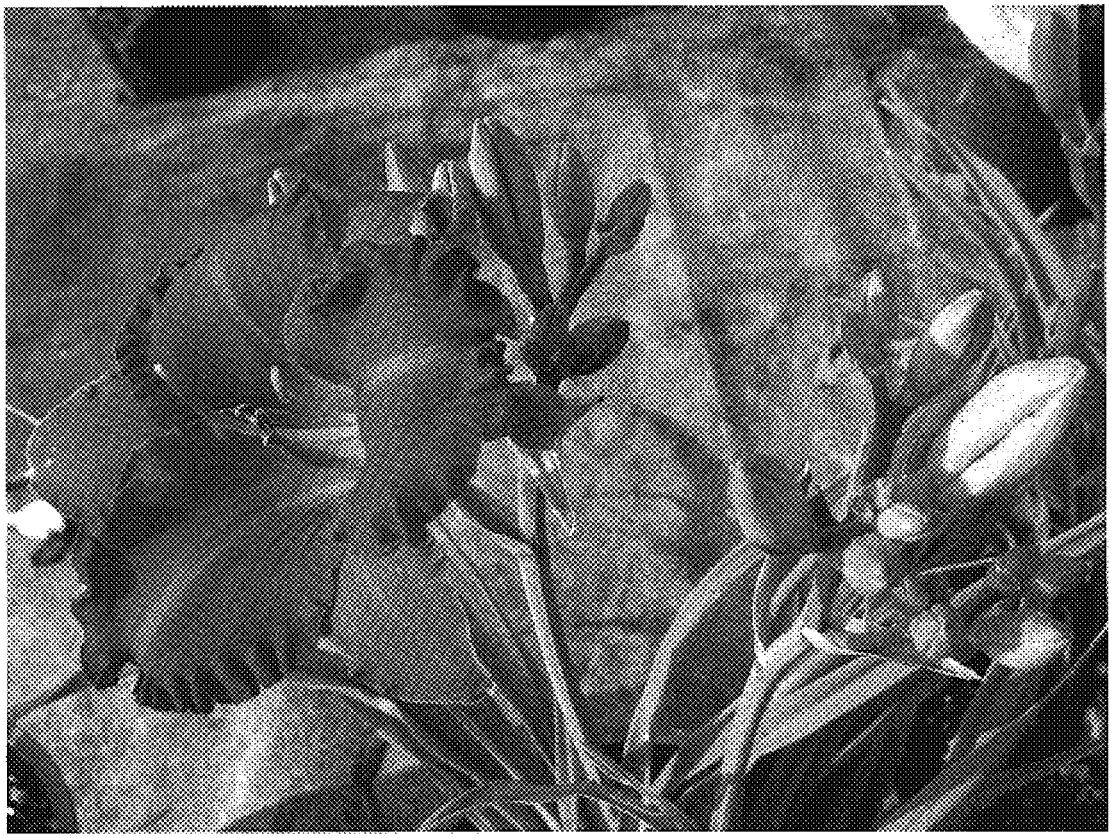

FIG. 3 — illustrates an additional view of a typical flower of the present invention as well as clusters of buds in various stages of development.

DETAILED DESCRIPTION

The chart used in the identification of the colors described herein is the R.H.S. Colour Chart of the Royal Horticultural Society, London, England. In some instances, more common color terms are provided and are to be accorded their usual dictionary significance. The original plant of the new cultivar is described when observed during August 2006 while growing at Bridgeton, N.J. U.S.A. under field growing conditions.

Plant:

*Height.*— Approximately 34 cm at an age of one year.

*Width.*—Approximately 64 cm at an age of one year.

*Foliage.*—Form: single stem, substantially erect fan-shaped plant having narrow arching, long, keeled, grass-like glabrous slightly textured leaves that are two-ranked at the base of the scape. Quantity: abundant, with a mature plant commonly having approximately 16 leaves per fan. Leaf Size: commonly approximately 2.5 cm in width on average, and approximately 58 cm in length on average. Leaf Shape: linear and long-keeled (as illustrated in FIG. 3) with entire margins. Texture: glabrous. Color: Yellow-Green Group 144A. Type: semi-evergreen with the plant commonly retaining some green coloration during the winter in U.S.D.A. Hardiness Zone No. 6b.

*Scape.*—Color Yellow-Green Group 146A. Length: commonly approximately 62 cm on average.

*Disease resistance.*—Typical of *Hemerocallis* with no problems having been observed to date.

Inflorescence:

*Bud.*—Form: modified oblanceolate (as illustrated in FIGS. 2 and 3). Size: on the day prior to opening commonly approximately 5.5 cm in length on average, and approximately 2 cm in width on average. Opening Rate: commonly approximately three hours on average. Peduncle Character: rigid and sturdy. Peduncle Color: Yellow-Green Group 144C.

*Flower.*—Size: commonly has a diameter of approximately 11.5 cm on average and a depth of approximately 6.5 cm on average. Borne: singly on the branchlets of a sturdy erect rachis which is ramulose. Each scape commonly has at least 30 peduncles, each of which divides into approximately 2 pedicels. Blooms Per Scape: commonly approximately 1 or 2 each day. Tepalage: each flower consists of six perianth segments wherein there are three outer tepals and three inner tepals all in an imbricated arrangement. Outer Tepal Shape: oblanceolate with slightly undulated entire margins and an acuminate apex. Outer Tepal Texture: slightly ribbed. Outer Tepal Size: commonly approximately 7.5 cm in length on average and approximately 3.5 cm in width on average. Outer Tepal Color: the overall area is Red Group 48A, and the base is Yellow-Green Group 151A. Outer Tepal Apex: somewhat mucronate. Inner Tepal Shape: generally ovate. Inner Tepal Texture: pie crust ruffled edge. Inner Tepal Size: commonly approximately 7.5 cm in length on average and approximately 4.5 cm in width on average. Inner Tepal Color: the overall area is Red Group 51B, and the base is Yellow-Green Group 144C. Blooming Habit: the flowers commonly bloom substantially continuously and the scape commonly is substantially continuously in bloom for up to approximately 90 days per year in Hardiness Zone No. 6. Effects of Weather: the flowers will withstand rain damage in view of the strength of the tepals. Lasting Quality: commonly at least 16 hours. As with other *Hemerocallis* cultivars known to the inventor, the flower color eventually fades somewhat during the day with the natural effects of environmental conditions and ongoing maturity. Fragrance: none.

*Reproductive Organs.*—Stamen Number: six per flower. Stamen Disposition: individually inserted at the summit of the perianth tube. Anther Disposition: introrse. Anther Size: approximately 5 mm in length. Anther Color: Black Group 202B. Filament Configuration: slender. Filament Length: commonly approximately 5 cm on average. Filament Color: Red Group 48A. Pollen Color: Yellow-Orange Group 23A. Pistil Number one per flower. Style Length: approximately 7.5 cm in length on average. Style Color: Red Group 48A. Stigma Color: Green-Yellow Group 1C. Ovaries: three-celled, oblong, and becoming a loculiedally three-valved capsule.

*Fruit.*—Configuration: the seed pod is in the form of an ovoid capsule. Color: at maturity commonly is Green Group 141B. Fertility: the seeds are fertile.

Hardiness: Cold tolerance is displayed in U.S.D.A. Hardiness Zone No. 5a, and heat tolerance is displayed in U.S.D.A. Hardiness Zone No. 8b.

I claim:

1. A new and distinct cultivar of *Hemerocallis* plant of the semi-evergreen type, substantially as herein shown and described, which:

(a) forms attractive ruffled bright rosy pink flowers having substantial substance, and a funnel-shaped form, (b) possesses a long blooming season with repeat blooming, (c) exhibits a propensity to readily display a plurality of fans, (d) readily forms a plurality of scapes per fan over the flowering season, and (e) commonly forms in excess of 30 buds per scape; substantially as illustrated and described.

* * * * *